(12) United States Patent
Dirac

(10) Patent No.: US 7,054,010 B2
(45) Date of Patent: May 30, 2006

(54) METHOD FOR THE OPTICAL ANALYSIS OF A FLUID

(75) Inventor: Holger Dirac, Birkeroed (DK)

(73) Assignee: Danfoss A/S, Nordborg (DK)

(*) Notice: Subject to any disclaimer, the term of this patent is extended or adjusted under 35 U.S.C. 154(b) by 357 days.

(21) Appl. No.: 10/257,734

(22) PCT Filed: Apr. 4, 2001

(86) PCT No.: PCT/DK01/00223

§ 371 (c)(1),
(2), (4) Date: Sep. 8, 2003

(87) PCT Pub. No.: WO01/79812

PCT Pub. Date: Oct. 25, 2001

(65) Prior Publication Data

US 2004/0061845 A1  Apr. 1, 2004

(30) Foreign Application Priority Data

Apr. 14, 2000 (DE) .............................. 100 28 067

(51) Int. Cl.
*G01N 21/05* (2006.01)

(52) U.S. Cl. ........................................ 356/440; 356/246

(58) Field of Classification Search ................ 356/246, 356/436, 440
See application file for complete search history.

(56) References Cited

U.S. PATENT DOCUMENTS

| | | | | |
|---|---|---|---|---|
| 3,609,048 A | * | 9/1971 | Strickler | 356/246 |
| 5,530,540 A | * | 6/1996 | Wyatt et al. | 356/246 |
| 5,780,754 A | | 7/1998 | Karlberg et al. | |
| 6,190,034 B1 | * | 2/2001 | Nielsen et al. | 366/336 |
| 2001/0055546 A1 | * | 12/2001 | Weigl et al. | 356/246 |

FOREIGN PATENT DOCUMENTS

| | | | |
|---|---|---|---|
| DE | 19536858 A1 | * | 4/1997 |
| EP | 0 486 747 | | 3/1991 |
| EP | 0 523 680 | | 7/1992 |
| EP | 0 523 680 A2 | | 1/1993 |
| GB | 1168608 | | 5/1968 |
| GB | 1360806 | | 9/1971 |
| WO | 97/13075 | | 4/1997 |

* cited by examiner

*Primary Examiner*—Richard A. Tosenberger
(74) *Attorney, Agent, or Firm*—Altera Law Group, LLC

(57) ABSTRACT

The invention concerns a method for the optical analysis of a fluid, in which the fluid that has a first refractive index, is surrounded by an auxiliary fluid with a second refractive index, the first refractive index being larger than the second refractive index and light being sent through the fluid. It is endeavoured to obtain an encapsulation of the fluid in the auxiliary fluid at low cost. For this purpose, firstly the auxiliary fluid is led into a measuring channel, until it is filled, and then lead the fluid into the auxiliary fluid within the cross section with a flow speed, which generates a parabolic flow profile.

7 Claims, 2 Drawing Sheets

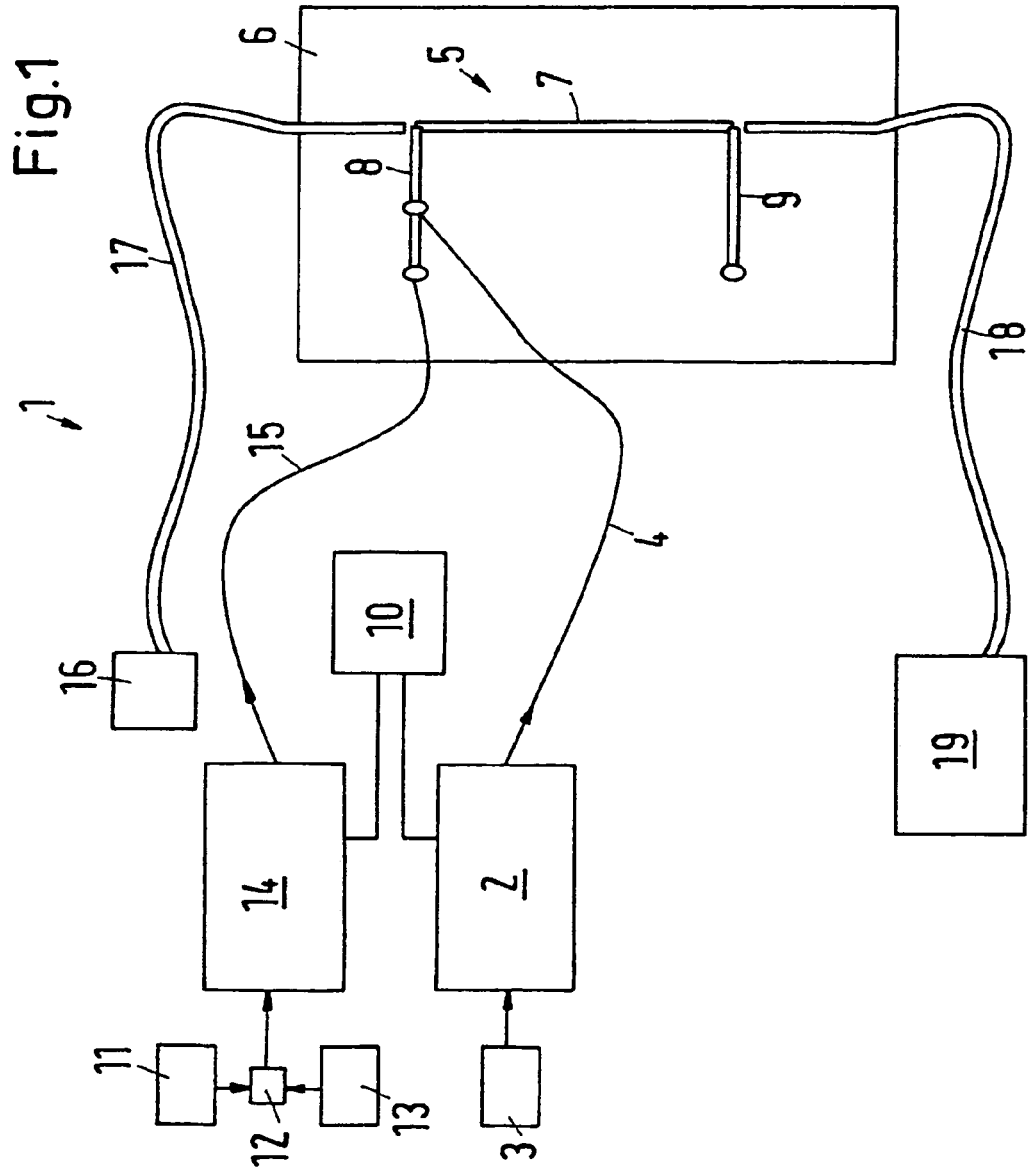

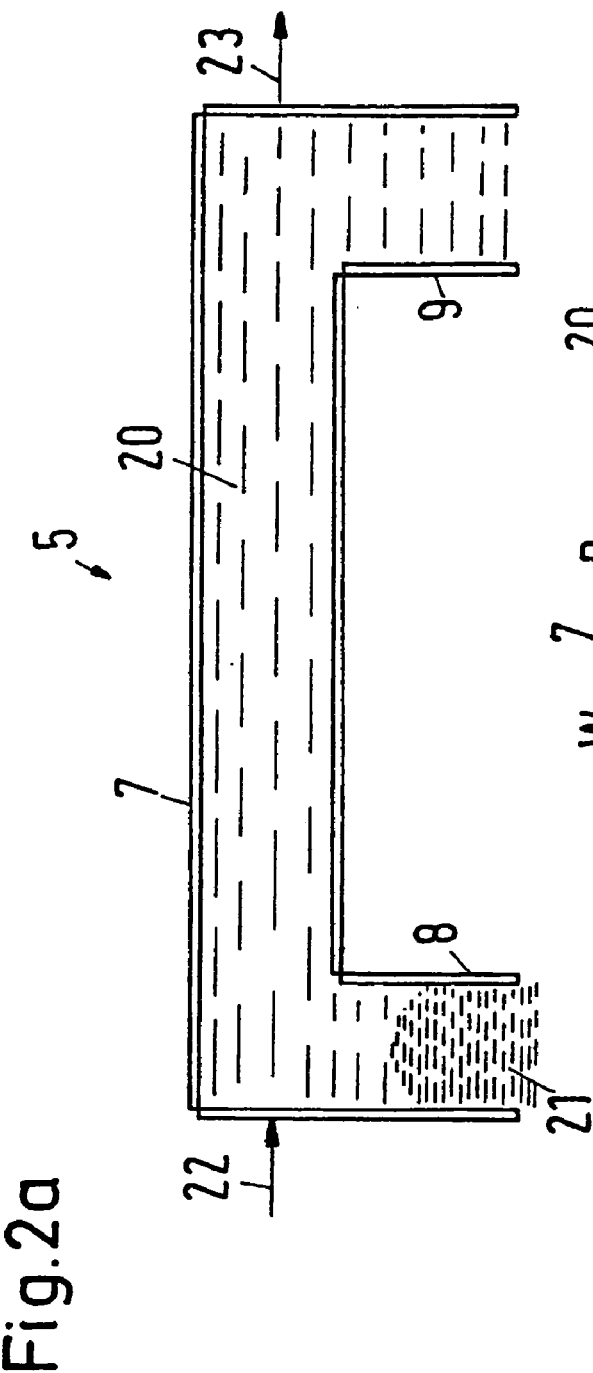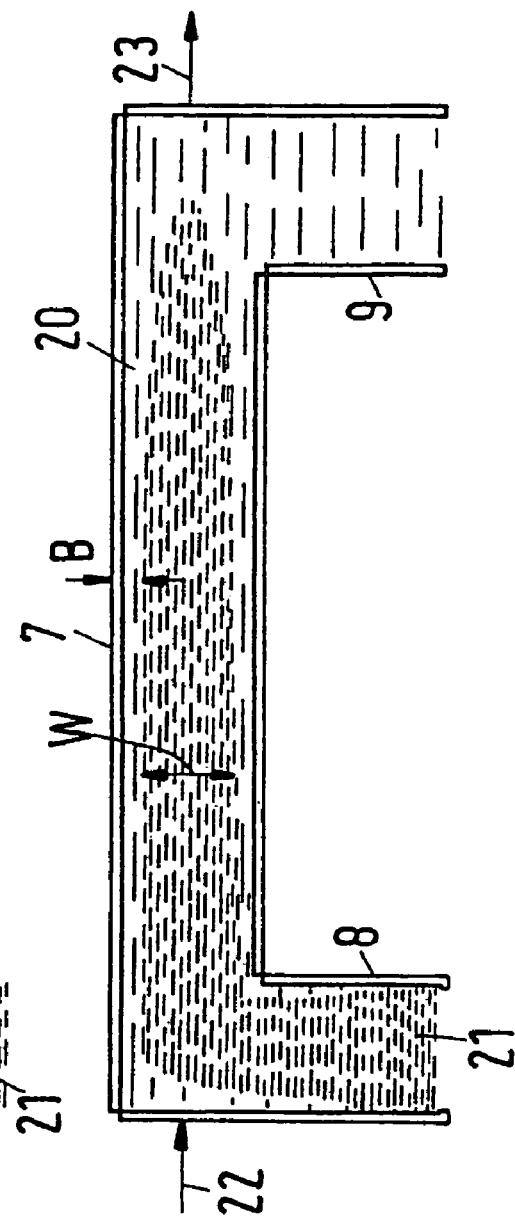
Fig.2a
Fig.2b

METHOD FOR THE OPTICAL ANALYSIS OF A FLUID

The invention concerns a method for the optical analysis of a fluid, in which the fluid that has a first refractive index, is surrounded by an auxiliary fluid with a second refractive index, the first refractive index being larger than the second refractive index and light being sent through the fluid.

Such a method is known from DE 195 36 858 A1. Such methods are particularly suited for light spectroscopic processes, in which the light is led through the fluid with a predetermined wave length or a predetermined wave length range. It can then be measured, how good the light gets through the fluid (transmission) or which spectral shares are absorbed (absorption). From these results, conclusions concerning certain substances can be made, the existence of which in the fluid is to be proved.

Encapsulating the fluid in an auxiliary fluid involves the advantage, among others, that the measuring channel is not impurified. Additionally, the optical properties of the measuring channel wall, for example, the reflection properties, are less important, so that cheaper materials can be used for the manufacturing of the measuring channel. The refractive indexes of fluid and auxiliary fluid can be adapted to each other in such a way that the introduced light is reflected at the boundary layer between fluid and auxiliary fluid, to remain in the fluid for as long as possible. With a suitable adaptation, a fluid optical conductor can be obtained, which has a total internal reflection. When a total internal reflection is available, the light is not merely reflected, but also literally led through the conductor.

In the method known from DE 195 36 858 A1, the fluid and the core fluid are introduced simultaneously in a laminating device, in which the fluids are laminated in relation to each other, though maintaining the same direction and the same speed. Thus, it is, in a manner of speaking, an active encapsulating process. This sort of encapsulation requires a relatively expensive device. Additionally, also the pumps supplying the fluids must meet high requirements, particularly with regard to the supply quantity accuracy.

The invention is based on the task of performing the encapsulation of the fluid in an auxiliary fluid at low cost.

With a method as mentioned in the introduction, this task is solved in that firstly the auxiliary fluid is led into a measuring channel, until it is filled, and secondly the fluid is led into the auxiliary fluid within the cross section with a flow speed, which results in a parabolic flow profile.

In this connection, it is not necessary that the fluid is supplied exactly in the centre of the cross section of the auxiliary fluid. It is sufficient that the supply occurs in the middle of the cross section. In this way, lamination of the two fluids is relatively easily realised. The fluid flowing in displaces the auxiliary fluid and flows through the auxiliary fluid in such a way that a layer of the auxiliary fluid, surrounding the fluid, remains between the wall of the measuring channel and the fluid. In this connection, the speed of the fluid is set so that a parabolic flow profile occurs. This flow profile occurs with a laminar flow, so that between the fluid and the auxiliary fluid a turbulence does not occur, but merely a boundary layer is created, on which the supplied light can be reflected due to the difference in the refractive indexes. The parabolic flow profile forms a peak that, being cone-shaped, pushes the auxiliary fluid away and penetrates it. The exact speed of the fluid depends on several parameters, for example on the density difference between the two fluids. Smaller cross sections or longer measuring channels require higher flow speeds. However, depending on the physical dimensions and the fluids chosen,-there is an upper limit on the flow speed, at which a turbulence appears and the laminar structure collapses. However, a person skilled in the art can easily find the required flow speed by performing a few tests. An additional advantage of the invention is that the requirements on the pump, transporting the fluid through the measuring channel, are less critical. In the known case, in which the fluids had to be laminated to each other with the same speed, the requirements, particularly with regard to synchronism, on the pumps were relatively high, as even small deviations in the pump speeds will have a critical effect on the laminate thickness and thus enable a local escaping of light from the fluid. With the new method, however, it must only be observed that the fluid is led into the auxiliary fluid at the right speed.

Preferably, the auxiliary fluid is water. Water, also pure water, is available to the required extent in most laboratories. The handling of it is simple. The refractive index of water is known or can easily be determined. Water is not aggressive in connection with many fluids, so that in most cases measuring results will not be distorted.

Preferably, the fluid is composed by a carrier and a sample. This is particularly advantageous, when the physical properties of the sample are similar to those of the auxiliary fluid, for example, when water is used as auxiliary fluid and the sample is sewage water from a purification plant, in which, for example, the contents of ammonium must be determined. By means of the carrier, the properties of the fluid can now be changed to such an extent that they deviate sufficiently from the physical properties of the auxiliary fluid.

It is particularly advantageous that the carrier is a fluid with a higher viscosity than that of the auxiliary fluid. For example, glycerol can be used as carrier, as it has a high viscosity. By means of the viscosity of the carrier, it is possible to get influence on the speed, at which the fluid must be led through the measuring channel.

Preferably, the light is sent through the measuring channel, as soon as the fluid is supplied. Thus, some kind of reference signal is obtained. The light will practically already reach its receiver, when only the auxiliary fluid is in the measuring channel. As soon as the fluid is added, the signal depending on the light will inevitably change. When changes no longer occur, it can be assumed that the measuring distance of the measuring channel is filled with fluid surrounded by the auxiliary fluid, and that in fact the subsequent measuring will take place on the predetermined length of the fluid. Thus, easily reproducible results can be obtained.

Advantageously, a U-shaped measuring channel with a base and two legs is used, the light being led through the base. This involves several advantages. Firstly, the light beam can get in and out through boundaries of the fluid, which are directed more or less vertically to the light beam. In this case, also with boundaries having heavily different refractive indexes, the reflection of the light beam remains low. Secondly, in this connection, at least the beginning of the measuring can be determined with a high reliability. The measuring can namely start, as soon as the peak of the fluid enters the base and crosses the light beam.

Preferably, the auxiliary fluid is replenished at a predetermined rate that depends on the supply rate of the fluid. This is particularly advantageous, when the fluid is available as "plugs" or blocks with a limited length. In this case, the next supply process can follow immediately after the passing of a sample. However, also with longer samples the careful supplying of the auxiliary fluid can be advantageous, to prevent the boundary layer between the wall of the measuring channel and the fluid from getting too thin.

The invention is useful in different measuring processes. Besides the absorption or transmission measurings described here, for example, also fluorescence or chemiluminescence processes can be used.

In the following, the invention is described on the basis of a preferred embodiment in connection with the drawings, showing:

FIG. 1 a schematic view of an analysis system

FIG. 2 various stages of a measuring process

FIG. 1 shows an analysis system 1, for example in the shape of a "lab on a chip" in micro-size. Such an analysis system will then only require a base area of a few square centimetres. The consumption of reagents and energy is extremely low, so that such analysis systems can also for a certain period of time be operated autonomously, that is, without supplying additional energy or reagents.

The analysis system 1 has a first pump 2, supplying an auxiliary fluid, having a low optical refractive index, from a tank 3 into an supply channel 4 for a measuring channel 5. The measuring channel can be cauterised or cut into a substrate 6, preferably of glass or plastic. For example, the measuring channel has a square cross section of 0.5 mm×0.5 mm. It is U-shaped and has a base portion 7 and two leg portions 8, 9, the leg portion 8 being an inlet channel and the leg portion 9 being an outlet channel. The base portion 7 forms a cyvette that has a length of 30 mm. Thus, the cyvette has a volume of 7.5 micro litres. The method used for filling the measuring channel 5 with water is insignificant.

A sample tank 11 (in stead of a sample tank, a sampling device may be provided, which takes water from a purification plant or produces a sample fluid by means of dialysis from the water of a purification plant) is connected with a mixing device 12 that mixes the sample with a carrier from a carrier tank 13. In the present case, the carrier is glycerol, which has a higher viscosity. The carrier is decisive for the size of the refractive index. Together, carrier and sample now form a fluid, which, in the following, is also called "core fluid". The refractive index of the core fluid is higher than that of water.

Through a second pump 14 and a supply channel 15, the core fluid is led to the inlet channel 8 and from there into the cross section. Like the rest of the measuring channel 5, the inlet channel 8 is filled With water.

The two pumps 2, 14 are controlled by a controlling device 10 that is able to synchronise the supply rates of the two fluids 20, 21 (FIG. 2*a*) in such a way that the desired parabolic course of the core fluid 21 in the fluid 20 occurs.

A light source 16 sends light with a certain wavelength range or a certain wave length, for example, from the UV-range or the IR-range, via a light conductor 17 into the cyvette 7. The outlet of the cyvette 7 is connected with a detector 19 via an additional light conductor 18. The detector 19 measures the absorption of the core fluid and based on this calculates the concentration of a substance in the sample, for example the ammonium content in the sewage.

FIG. 2 is a detailed view of the conditions in the measuring channel 5. The measuring channel 5 is filled with water 20 (FIG. 2*a*), and the core fluid 21 is supplied through the inlet channel 8. Simultaneously with the supply of the core fluid 21, the light source 16 and the detector 19 are activated, that is, the light source 16 sends out light extending in the longitudinal direction of the cyvette 7. This is marked by two arrows 22, 23. At the time shown in FIG. 2*a*, the light beam thus "measures" clean water.

In the embodiment shown, the core fluid is supplied at a speed of ten millilitres/hour. After approximately two seconds, the profile in FIG. 2*b* has been reached, and after approximately three seconds, the core fluid 21 has also passed the second leg or the outlet channel 9 of the measuring channel 5.

The fact that the light source 16 and the light sensor 19 are activated simultaneously with the supply of the core liquid 21, makes it possible to follow a signal course, and the final measuring can be made at the maximum of this signal, as at this stage the cyvette 7 is filled to the desired extent by the core fluid 21.

FIG. 2*b* shows the parabolic flow profile that has occurred due to the flow speed of the core fluid 21. The core fluid, having a diameter W, is surrounded by a laminar water layer with a thickness B. The thickness B is variable over the length of channel, however must exceed a minimum value, as otherwise the measuring signal will drop rapidly, as the light in the core fluid can escape through the wall of the cyvette 7. Also when the flow speed of the core fluid is too low, the thickness B may become too small due to the diffusion of the core fluid into the auxiliary fluid. Here, the cross section of the flow profile is shown as a parabola, however, in practice it has substantially the shape of a paraboloid. In a circular channel the profile is an almost ideal paraboloid. Also the water 20 can be replenished at a certain rate. When substantially maintaining a predetermined relation between the speeds of core fluid 21 and water 20, the parabolic peak shown occurs, which, like a cone, pushes the water 20 aside to surround the core fluid 21. This relation does not have to be strictly observed. The exact speed of the core fluid 21 depends on several parameters. The larger the differences between the densities of the two fluids are, the higher must the speed of the core fluid be, in order to prevent the core fluid from sinking to the bottom of the measuring channel 5. This is particularly important in systems, in which the fluids are to flow in horizontal channels. Also smaller cross sections or longer cyvettes 7 require higher flow speeds. Depending on the dimensions and the fluids chosen, there is an upper limit of the flow speed, at which turbulences occur and the laminar structure collapses. To prevent this from happening, the Reynolds figure should be lower than 2000.

The core fluid 21 can be a "plug" or a block with a limited length. In this case, the passing of each block will cause the system to revert to the original state, that is, the measuring channel 5 is filled with water 20 and is then ready to adopt the next sample. Due to the water layer between the sample and the measuring channel 5, a pollution of the measuring channel has not occurred.

However, the sample can also be available as a continuous, that is, longer block. Also in this case, merely the flow speed of the core fluid 21 must be set so that laminar conditions are maintained. In this case, a measuring can, for example, be performed over a longer period.

Finally, it is also possible, to supply laminated sections of the core fluid 21, in stead of such continuously extending sections, into the measuring channel 5. The principle of laminating such samples is known from, for example, DE 44 11 266 A1. Here, a particular opportunity of analysing appears. For example, the light can be led specifically through the "peaks" of the parabolic profiles to obtain an optical lens effect.

The invention claimed is:

1. Method for the optical analysis of a fluid, in which the fluid that has a first refractive index, is surrounded by an auxiliary fluid with a second refractive index, the first refractive index being larger than the second refractive index and light being sent through the fluid, wherein firstly the auxiliary fluid is led into a measuring channel, until it is filled, and secondly the fluid is led into the auxiliary fluid within the cross section with a flow speed, which results in a parabolic flow profile.

2. Method according to claim 1, wherein the auxiliary fluid is water.

3. Method according to claim 1, wherein the fluid is composed by a carrier and a sample.

4. Method according to claim 3, wherein the carrier is a fluid with a higher viscosity than that of the auxiliary fluid.

5. Method according to claim 1, wherein the light is sent through the measuring channel, as soon as the fluid is supplied.

6. Method according to claim 5, wherein a U-shaped measuring channel with a base portion and two leg portionss is used, the light being led through the base portion.

7. Method according to claim 1, wherein the auxiliary fluid is replenished at a predetermined rate that depends on the supply rate of the fluid.

* * * * *